United States Patent [19]

Irikura et al.

[11] Patent Number: 4,599,418

[45] Date of Patent: Jul. 8, 1986

[54] BENZOQUINOLIZINE CARBOXYLIC ACID DERIVATIVES, AND PROCESS FOR PREPARATION THEREOF

[75] Inventors: Tsutomu Irikura, Tokyo; Satoshi Murayama; Fjuio Iinuma, both of Tochigi, all of Japan

[73] Assignee: Kyorin Seiyaku Kabushiki Kaisha, Tokyo, Japan

[21] Appl. No.: 581,957

[22] Filed: Feb. 21, 1984

[30] Foreign Application Priority Data

Feb. 22, 1983 [JP] Japan .................. 58-28135

[51] Int. Cl.[4] .................. C07D 401/04; C07D 455/06; A61K 31/495
[52] U.S. Cl. .................................................. 544/361
[58] Field of Search .................. 544/361; 424/250

[56] References Cited

U.S. PATENT DOCUMENTS

| | | | |
|---|---|---|---|
| 4,399,134 | 8/1983 | Ishikawa et al. | 544/361 |
| 4,416,884 | 11/1983 | Ishikawa et al. | 544/361 |
| 4,429,127 | 1/1984 | Irikura et al. | 424/250 |

FOREIGN PATENT DOCUMENTS

| | | | |
|---|---|---|---|
| 2463771 | 2/1981 | France | 544/361 |
| 2091726 | 8/1982 | United Kingdom | 544/361 |

*Primary Examiner*—George F. Lesmes
*Assistant Examiner*—S. A. Gibson
*Attorney, Agent, or Firm*—Toren, McGeady, Stanger, Goldberg & Kiel

[57] ABSTRACT

New compounds effective as antibacterial agent are disclosed. These new compounds include 8-[4-(4-aminobenzyl)-1-piperazinyl]-9-fluoro-6,7-dihydro-5-methyl-1-oxo-1H,5H-benzo[ij]quinolizine-2-carboxylic acid, hydrates and acid addition salts thereof, and possess superior activities against gram-negative and gram-positive of aerobicbacteria.

1 Claim, No Drawings

BENZOQUINOLIZINE CARBOXYLIC ACID DERIVATIVES, AND PROCESS FOR PREPARATION THEREOF

BACKGROUND OF THE INVENTION

1. Field of the Invention

The present invention relates to new and useful benzoquinolizine carboxylic acid derivatives, useful as antibacterial agent and preparation process therefor.

2. Description of the Prior Art

Nalidixic acid, developed by Lesser et al. in 1962, has been widely known as antibacterial agent having potent activities against gram-negative of aerobicbacteria. Many new quinolone compounds related to nalidixic acid have been developed during the last few years. And, norfloxacin, one of these derivatives, possessing superior activities not only to gram-negative but also to gram-positive of aerobicbacteria has been developed.

The present inventors have made extensive studies earnestly to develop compounds having potent antibacterial activity not only against aerobicbacteria but also against obligate anaerobicbacteria, and invented new compounds having greater potencies and a broader antibacterial spectrum against both aerobicbacteria and obligate anaerobicbacteria than the prior art compounds, such as nalidixic acid and norflaxacin.

SUMMARY OF THE INVENTION

Namely, the new compounds according to the present invention firstly include 8-[4-(4-aminobenzyl)-1-piperazinyl]-9-fluoro-6,7-dihydro-5-methyl-1-oxo-1H,5H-benzo[ij]quinolizine-2-carboxylic acid (hereinafter abbreviated as Compound [I]), hydrates and acid addition salts thereof, having the formula;

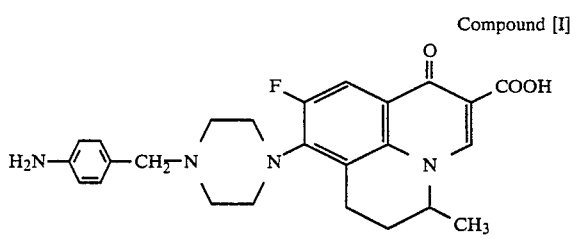

Compound [I]

DETAILED DESCRIPTION OF THE INVENTION

The Compound [I] of the present invention shows a striking broad spectrum in antibacterial activity against both of gram-negative and gram-positive aerobicbacteria, and gram-negative and gram-positive obligate anaerobicbacteria. Therefore, the Compound [I] is practically effective as antibacterial agent, applicable to new medicines to be administered for treatment of human deseases and also applicable to drugs for fishes and animals, and agricultural chemicals. The compounds of the present invention are prepared from 8-[4-(4-nitrobenzyl)-1-piperazinyl]-9-fluoro-6,7-dihydro-5-methyl-1-oxo-1H,5H-benzo[ij]quinolizine-2-carboxylic acid (hereinafter abbreviated as Compound [II]) by reduction, such as, for example, catalytic reduction by hydrogen in the presence of catalysts, such as, palladium, nickel and platinum, or reduction by metals such as zinc, tin, iron and aluminum amalgam, or reduction by metal ions, such as stannous ion and ferrous ion, for example, in the form of salts, and preferably, catalytic reduction, for example, by hydrogen in the presence of palladium on charcoal in acetic acid under normal pressure at room temperature.

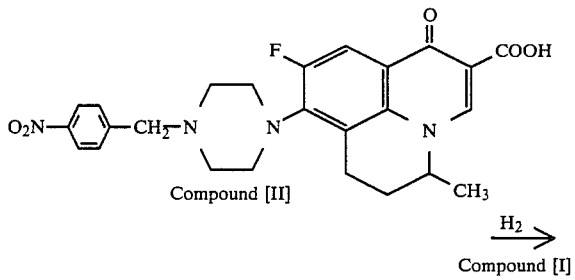

In addition, the Compound [II], the starting material, is also a novel compound, and is prepared, for example, by the following method. The Compound [II] is prepared by reaction of 9-fluoro-6,7-dihydro-5-methyl-1-oxo-8-(1-piperazinyl)-1H,5H-benzo[ij]quinolizine-2-carboxylic acid (hereinafter abbreviated as Compound [III]), or its acid addition salts with p-nitrobenzyl halide (preferably bromide or chloride) (hereinafter abbreviated as Compound [IV]) in an appropriate solvent, such as, for example, N,N-dimethylformamide, at a temperature range from room temperature to boiling points of solvents used, preferably, in the presence of an acid acceptor, such as triethylamine.

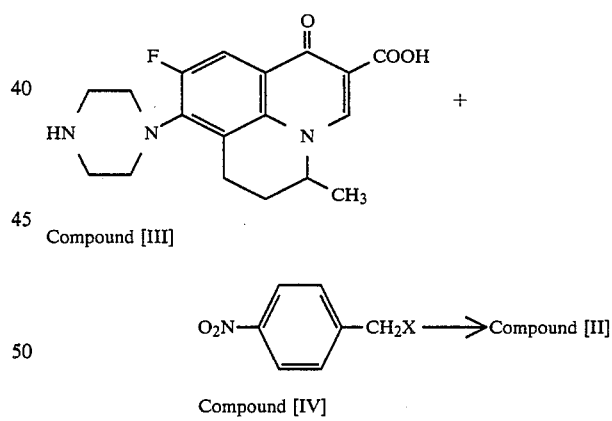

DESCRIPTION OF PREFERRED EMBODIMENTS

The present invention will be better understood from the following description of preferred embodiments.

EXAMPLE 1

Preparation of 8-[4-(4-nitrobenzyl)-1-piperazinyl]-9-fluoro-6,7-dihydro-5-methyl-1-oxo-1H,5H-benzo[ij]quinolizine-2-carboxylic acid (Compound [II])

A mixture of 9-fluoro-6,7-dihydro-5-methyl-8-(1-piperazinyl)-1-oxo-1H,5H-benzo[ij]quinolizine-2-carboxylic acid (Compound [III]), hydrochloride (1.1 g), p-nitrobenzyl bromide (Compound [IV]) (1.87 g) and triethylamine (1.46 g) in N,N-dimethylformamide (50 ml) was heated with stirring at 80°–90° C. for 10 hr. After evaporation of the solvent, water was added to the residue, and the aqueous mixture was extracted with chloroform. The chloroform layer was dried over anhydrous sodium sulfate and evaporated to dryness. The residue was recrystallized from a mixture of N,N-dimethylformamide and ethanol (2:1) to give 0.83 g (yield: 60%) of 8-[4-(4-nitrobenzyl)-1-piperazinyl]-9-fluoro-6,7-dihydro-5-methyl-1-oxo-1H, 5H-benzo[ij]quinolizine-2-carboxylic acid (Compound [II]) as pale yellow needles, m.p. 230°–233° C. (decompd.).

|  | C | H | N |
|---|---|---|---|
| Anal. Calcd. for $C_{25}H_{25}FN_4O_5$ | 62.49 | 5.24 | 11.66 |
| Found | 62.59 | 5.11 | 11.82 |

EXAMPLE 2

Preparation of 8-[4-(4-aminobenzyl)-1-piperazinyl-9-fluoro-6,7-dihydro-5-methyl-1-oxo-1H,5H-benzo[ij]quinolizine-2-carboxylic acid (Compound [I])

The Compound [II] (0.71 g), mixed with 10% palladium on charcoal (0.2 g) and acetic acid (25 ml), was hydrogenated with the calculated volume of hydrogen under normal pressure at room temperature. After the calculated volume of hydrogen was taken up, palladium on charcoal was filtered, and the filtrate was concentrated to dryness. The residue was dissolved in a small amount of water, and neutralized with 10% sodium hydroxide solution. The resulting precipitate was collected, dried, and purified by column chromatography on silicagel using a mixture of chloroform and ethanol (10:1) as the developing solvent. The purified product was recrystallized from ethanol to give 0.25 g (yield: 37.1%) of 8-[4-(4-aminobenzyl)-1-piperazinyl]-9-fluoro-6,7-dihydro-5-methyl-1-oxo-1H,5H-benzo[ij]quinolizine-2-carboxylic acid (Compound [I]) as pale yellow needles, m.p. 215.5°–217.5° C. (decompd.).

|  | C | H | N |
|---|---|---|---|
| Anal. Calcd. for $C_{25}H_{27}FN_4O_3 \cdot \frac{1}{2}H_2O$ | 65.77 | 6.11 | 12.27 |
| Found | 65.92 | 5.93 | 12.21 |

EXPERIMENT 1

The antibacterial activity of the Compound [I] of the present invention was assayed by the standard agar dilution streak method against aerobicbacteria and obligate anaerobicbacteria (Chemotherapy Vol.22, No.6, pp.1126–1128 (1974): Vo.27, No.3, pp.559–560 (1979). The results are shown in Table 1 and Table 2.

TABLE 1

| Antibacterial Activity Against Aerobicbacteria | | | | |
|---|---|---|---|---|
| | | Minimum Inhibitory Concentration (μg/ml) | | |
| Organisms | Gram | Compound (I) | NA | NFLX |
| Bacillus subtilis PCI219 | + | 0.05 | 6.25 | 0.20 |
| Staphylococcus aureus 209P | + | 0.05 | 100 | 0.78 |
| Streptococcus pyogenes IID692 | + | 0.20 | >100 | 3.13 |
| Streptococcus pyogenes S-8 | + | 0.10 | >100 | 1.56 |
| Streptococcus faecalis IID682 | + | 0.39 | >100 | 3.13 |
| Escherichia coli NIHJ JC-2 | − | 0.20 | 3.13 | 0.05 |
| Escherichia coli ATCC10536 | − | 0.20 | 3.13 | 0.05 |
| Proteus vulgaris IFO3167 | − | 0.78 | 3.13 | 0.05 |
| Salmonella enteritidis IID604 | − | 1.56 | 12.5 | 0.10 |
| Shigella sonnei IID969 | − | 0.39 | 1.56 | 0.05 |
| Pseudomonas aeruginosa V-1 | − | 12.5 | 100 | 0.78 |
| Pseudomonas aeruginosa IFO12689 | − | 25 | >100 | 1.56 |

NA: Nalidixic acid
NFLX: Norfloxacin

TABLE 2

| Antibacterial Activity Against Anaerobicbacteria | | | | |
|---|---|---|---|---|
| | | Minimum Inhibitory Concentration (μg/ml) | | |
| Organisms | Gram | Compound (I) | NA | NFLX |
| Bacteroides fragilis GM7000 | − | 1.56 | >25 | >25 |
| Bacteroides fragilis 0558 | − | 0.78 | >25 | >25 |
| Bacteroides distasonis 8503 | − | 3.13 | >25 | 12.5 |
| Bacteroides thetaiotaomicron 0661 | − | 6.25 | >25 | >25 |
| Bacteroides vulgatus | − | 0.78 | >25 | >25 |
| Bacteroides bivius | − | 1.56 | >25 | >25 |
| Bacteroides melaninogenicus GAI0410 | − | 0.78 | >25 | 6.25 |
| Fusobacterium necrophorum S-45 | − | 0.20 | >25 | 3.13 |
| Fusobacterium varium | − | 12.5 | >25 | >25 |
| Fusobacterium nucleatum | − | 1.56 | >25 | 25 |
| Eubacterium limosum | + | 3.13 | 25 | 6.25 |
| Propionibacterium acnes 11828 | + | 3.13 | >25 | 1.56 |
| Peptococcus maggnus | + | 0.20 | >25 | 1.56 |
| Clostridium difficile | + | 12.5 | >25 | >25 |
| Clostridium perfringens | + | 0.39 | 12.5 | 1.56 |
| Clostridium ramosum | + | 1.56 | >25 | >25 |

NA: Nalidixic acid
NFLX: Norfloxacin

As shown in Table 1 and Table 2, the Compound [I] is more active than nalidixic acid and norfloxacin against obligate anaerobicbacteria (both gram-negative and gram-positive bacteria) and gram-positive of aerobicbacteria, and nalidixic acid against gram-positive of aerobicbacteria. As illustrated above, the present compounds possess greatly broader potent antibacterial spectrums against both aerobic and obligate anaerobicbacteria and are particularly effective as antibacterial agent.

What we claim:
1. 8-[4-(4-Aminobenzyl)-1-piperazinyl]-9-fluoro-6,7-dihydro-5-methyl-1-oxo-1H,5H-benzo[ij]-quinolizine-2-carboxylc acid, hydrates and acid addition salts thereof.

* * * * *

UNITED STATES PATENT AND TRADEMARK OFFICE
CERTIFICATE OF CORRECTION

PATENT NO. : 4,599,418

DATED : July 8, 1986

INVENTOR(S) : Tsutomu Irikura, et al

It is certified that error appears in the above-identified patent and that said Letters Patent is hereby corrected as shown below:

In the heading of the Patent, it should read:

-- [75] Inventors: Tsutomu Irikura, Tokyo; Satoshi

Murayama; Fujio Iinuma, both of

Tochigi, all of Japan

Signed and Sealed this

Twenty-eighth Day of October, 1986

[SEAL]

Attest:

DONALD J. QUIGG

Attesting Officer     Commissioner of Patents and Trademarks